US00PP26171P2

(12) United States Plant Patent
Kordes

(10) Patent No.: US PP26,171 P2
(45) Date of Patent: Dec. 1, 2015

(54) HYBRID TEA ROSE PLANT NAMED 'KORLADCHER'

(50) Latin Name: *Rosa hybrida*
Varietal Denomination: KORladcher

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 121 days.

(21) Appl. No.: 13/987,680

(22) Filed: Aug. 20, 2013

(51) Int. Cl.
*A01H 5/02* (2006.01)

(52) U.S. Cl.
USPC ..... Plt./138

(58) Field of Classification Search
USPC ..... Plt./138
See application file for complete search history.

(56) References Cited

PUBLICATIONS

Help Me Find, 2015.*

* cited by examiner

*Primary Examiner* — Keith O. Robinson

(57) ABSTRACT

A new and distinct variety of rose with long lasting, novel dark pink flowers, and attractive foliage with excellent disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORladcher'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2002. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORladcher'.

SUMMARY OF THE INVENTION

The new rose plant may be distinguished from its seed parent, an un-named seedling, by the following combination of characteristics:

1. 'KORladcher' has dark pink flowers, whereas the un-named seedling has coral flowers.

2. 'KORladcher' has a very double petal count, whereas the un-named seedling has a double petal count.

The new rose plant may be distinguished from its pollen parent, an un-named seedling, by the following combination of characteristics:

1. 'KORladcher' has a medium size flower, whereas the un-named seedling has a small size flower.
2. 'KORladcher' has an upright to bushy habit, whereas the un-named seedling has a compact habit.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORladcher' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORladcher' was selected in May 2003 from the seedling beds to be asexually propagated for further evaluation. The first asexual propagation of 'KORladcher' was done by budding in July 2003 at the inventor's nursery in Offenseth-Sparrieshoop, Germany.

These initial and other subsequent propagations conducted in controlled environments demonstrate that 'KORladcher' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORladcher' taken from a 2-year-old plant growing in a nursery in Jackson County, Oreg.

DETAILED BOTANICAL DESCRIPTION

The following is a description of 'KORladcher', as observed growing in June 2013 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORcoluma', a rose variety from the same inventor described and illustrated in U.S. Plant Pat. No. 17,047 and issued on Aug. 22, 2006 are compared to 'KORladcher' in Chart 1.

CHART 1

| Characteristic | 'KORladcher' | 'KORcoluma' |
|---|---|---|
| Flower color | Dark pink | Red |
| Petal count | 55-65 | 25-30 |
| Plant habit | Upright to bushy | Compact and bushy |

Parents:

*Seed parent*.—An un-named seedling.

*Pollen parent*.—An un-named seedling.

Classification:

*Botanical classification*.—*Rosa hybrida* 'KORladcher'.

*Commercial classification*.—Hybrid Tea rose.

FLOWER AND FLOWER BUD

Blooming habit: Continuous. Prolific.

Flower bud:

*Size*.—Upon opening, 23-30 mm in length from base of receptacle to distal end of bud and 18 mm diameter at its widest point.

*Bud form*.—Long. Pointed ovoid.

*Bud color*.—As sepals first unfold, bud color is Red Group 53B. When ¼ open, the upper surface of petals is between Red Group 51A and Red Group 53C, and the lower surface is Red Group 53C.

*Sepals*.—Color: Upper surface Yellow-Green Group 146D. Lower surface Yellow-Green Group 146C. Intonations of Greyed-Purple Group 185A present on 85% of surface. Size: Average 25-35 mm (l)×12-15 mm (w). Shape: Moderate foliaceous appendages on 3 of the five sepals. Apex: Cirrose. Base: Flat at union with receptacle. Quantity: Five. Surface texture: Upper side: Heavily pubescent. Lower surface: Lightly pubescent. Margins: Pubescent with occasional stipitate glands. Stipitate glands: Limited.

Flower bloom:

*Fragrance*.—Light.

*Duration*.—On the plant 3-6 days. As a cut flower, 4-5 days. Senesced petals drop away cleanly.

*Size*.—Medium for a hybrid tea rose. When open, the average flower diameter is 100 mm and the average flower height is 60 mm.

*Form*.—Shape of flower when viewed from the side: Upon opening, upper part: Convex. Upon opening, lower part: Flattened convex. Open flower, upper part: Flattened convex. Open flower, lower part: Flattened convex.

*Color*.—Upon opening, petals: Outermost petals: Outer Side: Red-Purple Group N57C. Inner Side: Red-Purple Group 58B. Innermost petals: Outer Side: Red Group 55A. Inner Side: Red Group 52B. Upon opening, basal petal spots: Basal petal spot, outermost petals: Outer Side: Green-Yellow Group 1C. Inner Side: Green-Yellow Group 1B. Basal petal spot, innermost petals: Outer Side: Green-Yellow Group 1A. Inner Side: Green-Yellow Group 1A. After opening, petals: Outermost petals: Outer Side: Red-Purple Group 61C. Inner Side: Red-Purple Group 58B with occasional center stripe of White Group 155C. Innermost petals: Outer Side: Red-Purple Group 61D. Inner Side: Red-Purple Group 58B. After opening, basal petal spots: Basal petal spot, outermost petals: Outer Side: White Group N155C. Inner Side: Green-White Group 157C. Basal petal spot, innermost petals: Outer Side: White Group N155C. Inner Side: Green-White Group 157B.

General tonality: On open flower Red Group 53D. No change in the general tonality at the end of the 4$^{th}$ day. Afterwards, general tonality is Red-Purple Group 62C.

Petals:

*Petal count*.—Very Double.

*Average range*.—Approximately 55-65 petals under normal conditions.

*Petal reflex*.—Petals reflex slightly.

*Petal margin*.—Entire.

*Petal shape*.—Obovate. Apex: Obtuse. Base: Obtuse.

*Petal size*.—40-65 mm (l)×50-70 mm (w).

*Thickness*.—Average.

*Petal arrangement*.—Not formal.

*Texture*.—Upper and Lower Surfaces: Slightly rugose.

Petaloids:

*Petaloid count*.—Average of 8-12 per flower.

*Petaloid size*.—10-35 mm (l)×5-35 mm (w).

*Petaloid color*.—Inner side: Red-Purple Group N57A. Outer side: Red-Purple Group 58C.

*Petaloid texture*.—Outer and Inner Sides: Leathery.

*Margins*.—Entire to indented, with some highly irregular.

*Petaloid shape*.—Obovate, spatulate and oblanceolate. Apex: Acute to obtuse. Base: Attenuate.

Reproductive organs:

*Pistils*.—Abundant. Approximately 70 present. Stigmas: Location: Slightly superior in position to anthers. Color: Greyed-Yellow Group 160B. Styles: Length: About 15 mm long. Color: Green-White Group 157A. Intonations: Red-Purple Group N66A.

*Stamens*.—Approximately 90 on average and regularly arranged. Anthers: Size: Average 3 mm (l)×0.5-1.0 mm (w). Color: Yellow-Orange Group 20B. Pollen: Generally present. Color: Greyed-Orange Group 163A. Filaments: Color: Yellow Group 2A. Length: 8 mm.

*Receptacle*.—Surface: Lacking fine hairs and stipitate glands. Color: Yellow-Green Group 146C. Intonations: Greyed-Purple Group 187B. Shape: Mostly funnel-shaped. Texture: Smooth. Size: 9-15 mm (h)× 15-18 mm (w).

*Peduncle*.—Surface: Glabrous. Length: 50-75 mm average length. Diameter: 4-5 mm average diameter. Color: Yellow-Green Group 146C. Intonations: Greyed-Purple Group 183A to Greyed-Purple Group 183C. Strength: Strong. Borne: Singularly.

*Pedicel*.—Surface: Glabrous. Length: 50-75 mm average length. Diameter: 4-5 mm average diameter. Color: Yellow-Green Group 146C. Intonations: Greyed-Purple Group 183A to Greyed-Purple Group 183C. Strength: Strong. Borne: Singularly.

THE PLANT

Growth: Moderately vigorous.

Plant habit: Upright to bushy. When grown as a field plant, the average plant height is 120 cm and the average plant width is 80 cm.

Stems:

*Stem color*.—Young wood: Yellow-Green Group 146B. Older wood: Yellow-Green Group 146B.

*Intonations*.—Greyed-Purple Group 183B prevalent on new wood.

*Stem surface texture*.—Young wood: Smooth. Older wood: Smooth.

Prickles: Present.

*Incidence*.—Average of 10 per each 10 cm of stem.

*Size*.—Average length: 5 mm.

*Color*.—Immature prickles: Greyed-Red Group 182A to Greyed-Red Group 182B. Mature prickles: Greyed-Yellow Group 161C.

*Shape*.—Concave.

*Texture*.—Smooth.

Leaves: Normally 5 leaflets on normal leaves in middle of the stem.

*Venation pattern*.—Pyramidal net pattern.

*Leaf size*.—150-180 mm (l)×110-130 mm (w).

*Abundance*.—Average.

*Texture*.—Upper Surface: Smooth. Lower Surface: Smooth.

*Leaflets*.—Size: Average size of the terminal leaflet is 70 mm (l)×35 mm (w). Shape: Ovate. Base: Broadly obtuse. Apex: Acute. Margins: Serrated. Surface: Upper side of leaflet: Semi-glossy. Under side of leaflet: Matte. Texture: Upper side of leaflet: Smooth. Under side of leaflet: Smooth. Color, mature foliage: Upper Leaflet Surface: Yellow-Green Group 147A. Lower Leaflet Surface: Yellow-Green Group 147B. Color, juvenile foliage: Upper Leaflet Surface: Yellow-Green Group 146A. Lower Leaflet Surface: Yellow-Green Group 146B. Anthocyanin intonation: Greyed-Red Group 178A. Location: On juvenile foliage, particularly along leaflet margins. Arrangement: Odd pinnate. Venation: Reticulate.

Stipules:

*Size*.—25 mm (l)×7 mm (w).

*Stipule color*.—Yellow-Green Group 146C.

*Anthocyanin*.—Greyed-Red Group 181B present only on juvenile foliage.

*Stipitate glands*.—Limited numbers along margin.

*Texture*.—Smooth.

*Shape*.—Apex: Apiculate. Base: Flat.

Petiole:

*Length*.—Average 20-25 mm.

*Diameter*.—Average 1-1.5 mm.

*Petiole color*.—Yellow-Green Group 146A. Underneath: Yellow-Green Group 146B.

*Margins*.—Limited numbers of stipitate glands.

*Anthocyanin*.—Greyed-Purple Group 187B on juvenile foliage.

*Prickles*.—Present.

*Texture*.—Upper side: Leathery. Lower side: Smooth.

Petiole rachis:

*Length*.—Average 55 mm.

*Diameter*.—Average 2 mm.

*Color*.—Yellow-Green Group 146C. Anthocyanin present on juvenile tissue: Greyed-Purple Group 187B.

*Margins*.—Very limited stipitate glands.

*Prickles*.—A few small prickles underneath at leaflet attachment.

*Texture*.—Smooth.

Hips/seed formation: None observed.

Winter hardiness: To date, the variety has been grown successfully in Zone 6A.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

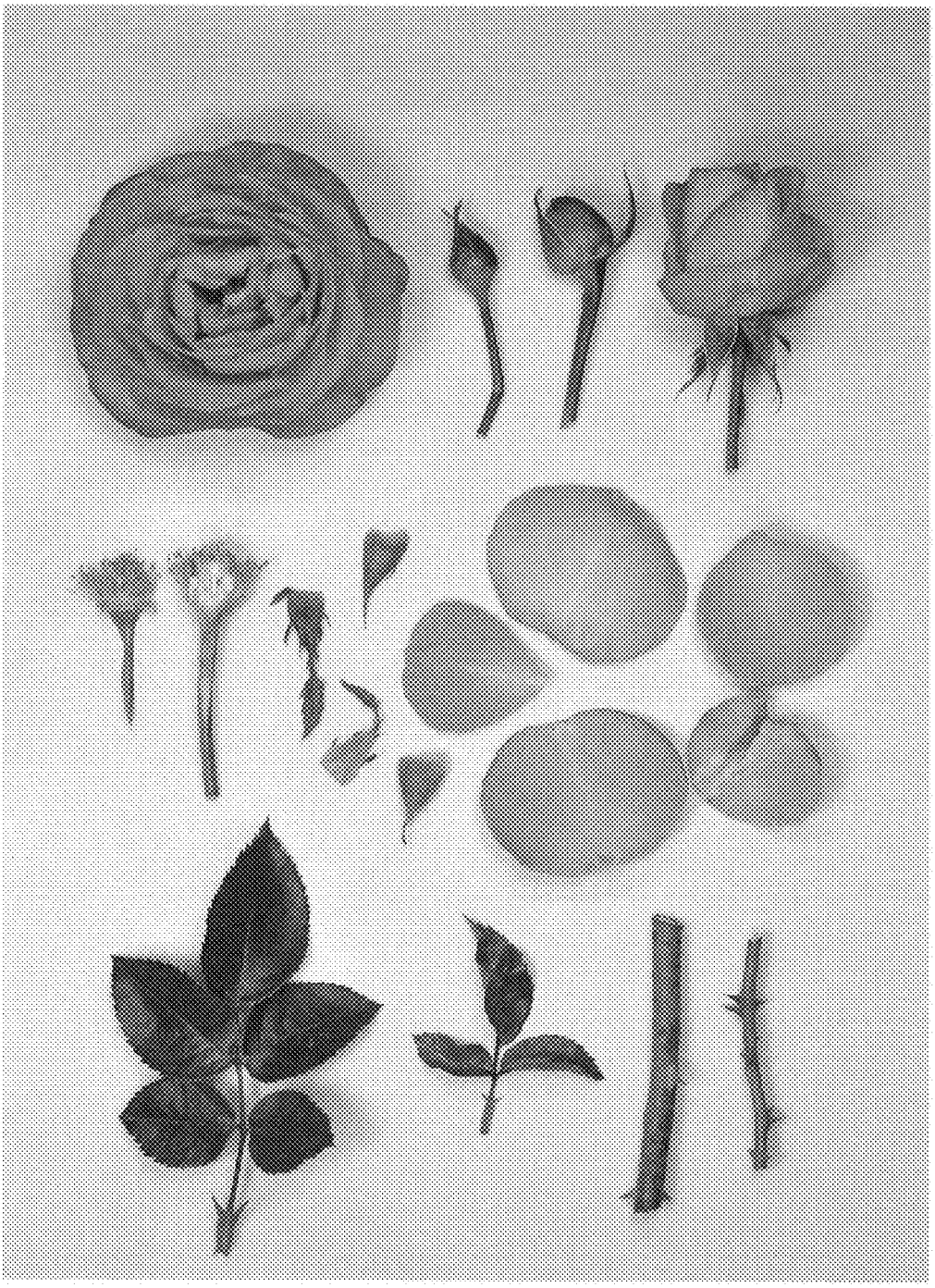

* * * * *